United States Patent [19]

Passafiume et al.

[11] 4,216,687
[45] Aug. 12, 1980

[54] METHOD FOR SHAPING AND/OR CUTTING BATTS OF LOOSELY COMPACTED FIBROUS MATERIALS

[75] Inventors: Anthony Passafiume, Burbank; Clarence F. Lamber, Country Hills Club; William Dickover, Richton Park, all of Ill.

[73] Assignee: Johnson & Johnson, New Brusnwick, N.J.

[21] Appl. No.: 888,818

[22] Filed: Mar. 21, 1978

[51] Int. Cl.² ............................................. B26F 1/26
[52] U.S. Cl. ................................. 83/26; 83/53; 83/177; 83/300; 83/333; 264/160
[58] Field of Search ............... 264/89, 93, 90, 92, 264/119, 284, 160, 146, 163; 28/104, 116, 118; 19/161.1; 26/7; 83/22, 53, 177, 925 CC, 922, 918, 26

[56] References Cited

U.S. PATENT DOCUMENTS

| | | | |
|---|---|---|---|
| 2,464,301 | 3/1949 | Francis, Jr. | 264/119 |
| 2,776,451 | 1/1957 | Chavannes | 264/90 |
| 2,862,251 | 12/1958 | Kalwaites | 264/119 |
| 2,985,050 | 5/1961 | Schwacha | 83/53 |
| 3,054,148 | 9/1962 | Zimmerli | 264/90 |
| 3,088,859 | 5/1963 | Smith | 264/119 |
| 3,113,349 | 12/1963 | Nottebohm et al. | 264/119 |
| 3,136,649 | 6/1964 | Keahey, Jr. | |
| 3,212,378 | 10/1965 | Rice | 83/53 |
| 3,214,819 | 11/1965 | Guerin | 264/119 |
| 3,526,162 | 9/1970 | Willcox | 83/177 |
| 3,532,014 | 10/1970 | Franz | 83/53 |
| 3,543,619 | 12/1970 | Hellmer et al. | 264/161 |
| 3,756,106 | 9/1973 | Chadwick et al. | 83/177 |
| 3,851,356 | 12/1974 | Savich | 28/116 |
| 3,877,334 | 4/1975 | Gerber | 83/53 |
| 3,927,591 | 12/1975 | Gerber | 83/177 |
| 3,978,748 | 9/1976 | Leslie et al. | 83/53 |
| 3,996,825 | 12/1976 | Terry | 83/53 |
| 4,006,656 | 2/1977 | Shinomiya | 83/177 |
| 4,007,652 | 2/1977 | Shinomiya | 83/177 |

FOREIGN PATENT DOCUMENTS 2330195 1/1975 Fed. Rep. of Germany ............ 83/177

*Primary Examiner*—James B. Lowe

[57] ABSTRACT

Method for shaping and/or cutting batts of loosely compacted fibrous material into individual panels of specific shapes without ragged edges or hard-cut edges. A pair of rolls rotating in opposite directions, with high-pressure air blown from the surface of one roll to a recessed portion of the other in a spaced apart nip area used to carry out the method.

7 Claims, 4 Drawing Figures

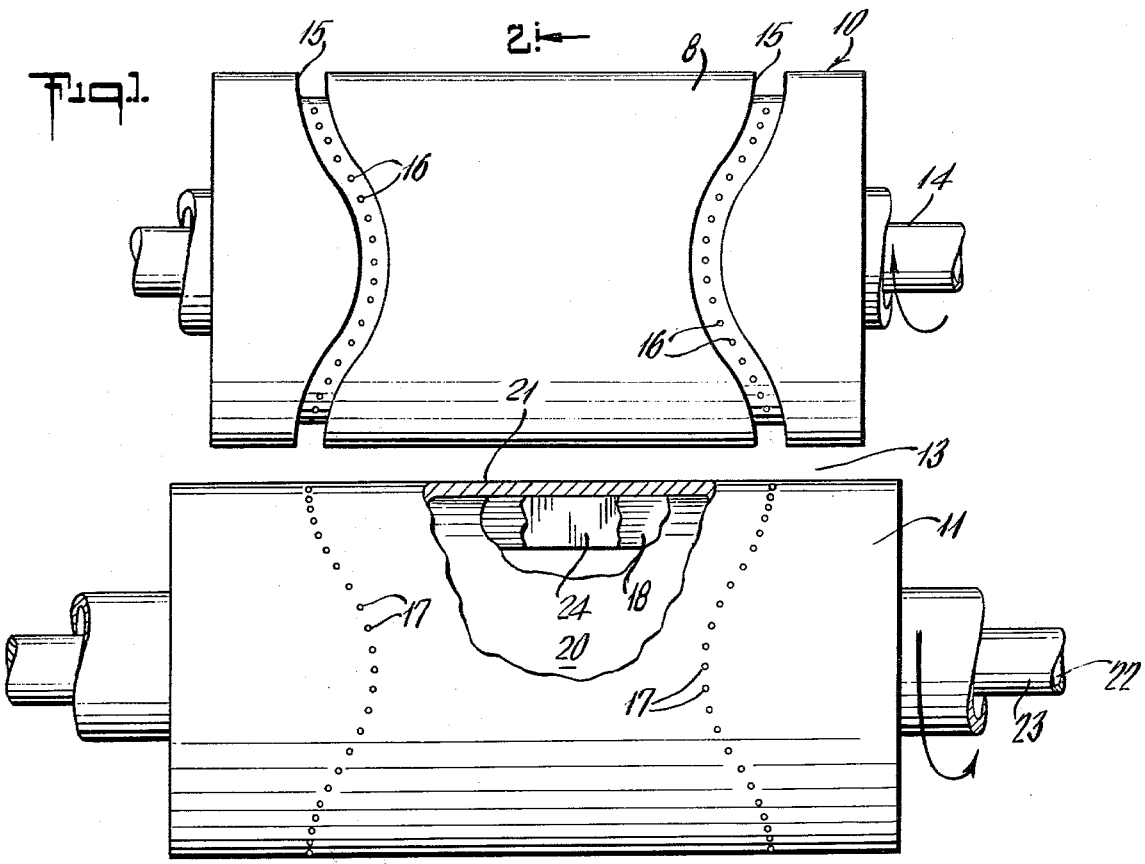
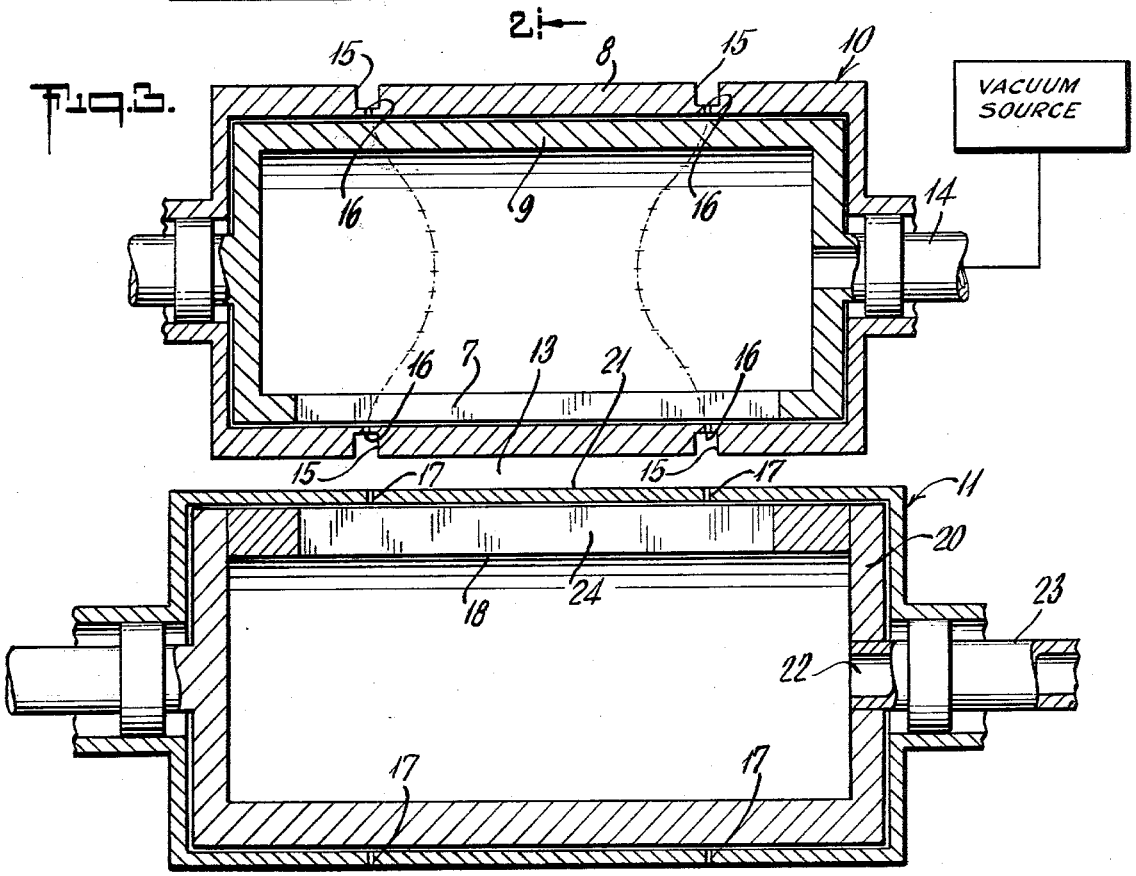

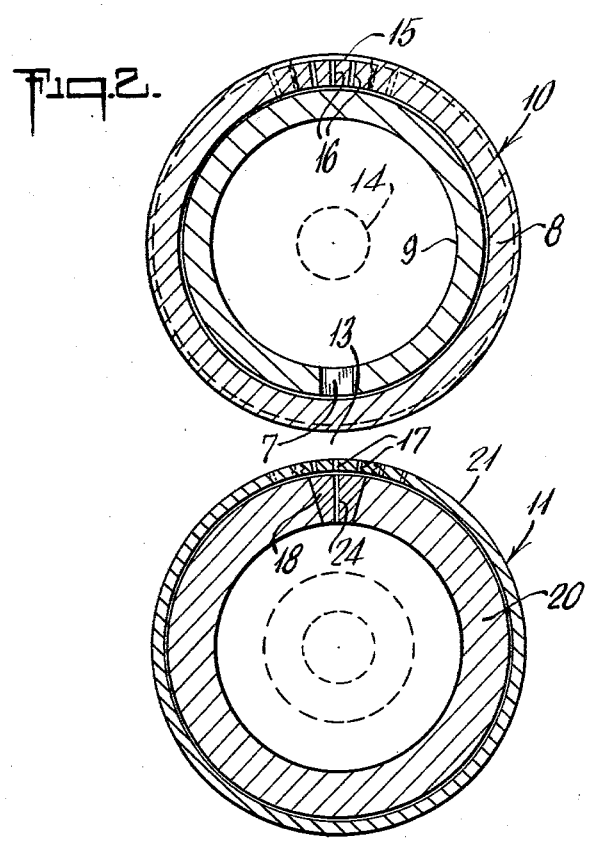
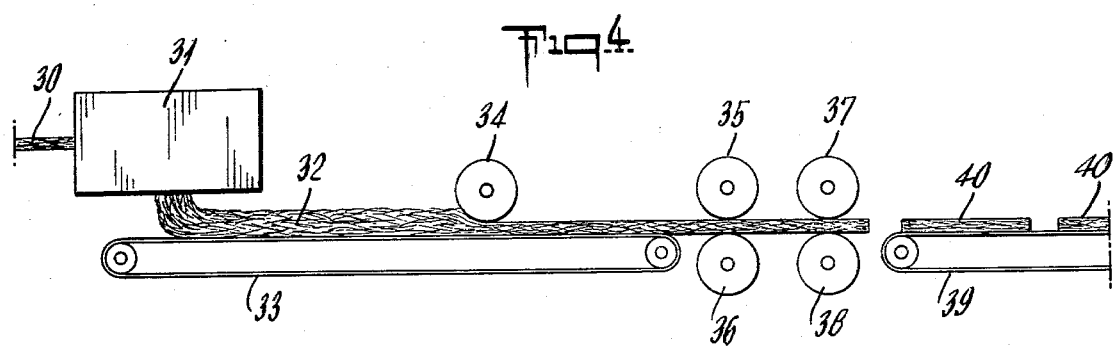

METHOD FOR SHAPING AND/OR CUTTING BATTS OF LOOSELY COMPACTED FIBROUS MATERIALS

BACKGROUND OF THE INVENTION

Many absorbent products, such as disposable diapers, sanitary napkins and the like, include an absorbent batt or panel. The absorbent batt is formed of loosely compacted short fibers, such as wood pulp fibers, or cotton linters, or mixtures thereof, and the like. The batt is produced by taking a source of short fibers such as a pulpboard and grinding the board and individualizing the fibers therein using a grinding mill. The individualized fibers are collected on a screen or other permeable means in the form of a layer of loosely associated short fibers. The layer is usually lightly compacted to provide some integrity.

In some absorbent products, a batt of a specific shape may be desired. In the prior art, shaped batts have been produced by forming the loose fibrous batt into the desired shape as the fibers are being laid on a screen or permeable means or by the usual technique of die-cutting or blade-cutting a rectangular batt.

What we have discovered is an improved method and apparatus for shaping batts of loosely compacted short fibers including cutting a continuous batt of such fibers into individual sections. Our new and improved method and apparatus will form and cut such batt at very high rates of speed and is economical. Both attributes are important in the production of disposable products such as disposable diapers. Furthermore, our new and improved method and apparatus will form any desired shape and forms the shape without either ragged edges or hard-cut edges which is often the case with prior art techniques. Our new and improved method and apparatus produces smooth uniform edges in the final batt with a minimum of loss of material.

SUMMARY OF THE INVENTION

In accordance with the present invention, the method of forming shaped batts of loosely compacted fibrous material comprises passing a batt of such fibrous material through the nip formed by a pair of spaced apart moving surfaces. The surfaces and batt move in the same direction and at the same speed. As the batt passes through the nip, high-pressure air is passed from one of the surfaces to the other surface in a pattern to produce the desired shape.

Apparatus for carrying out the above-described method comprises a pair of rolls rotating in opposite directions. The axes of the rolls are parallel. The rolls are disposed adjacent one another in spaced apart relationship to form a nip between the outer periphery of the rolls. One of the rolls has a recessed pattern disposed about its periphery in the shape desired to be produced in the batt. The other of said rolls comprises a stationary inner shell and a rotatable outer shell. The inner shell has a slot disposed transverse of its periphery at the position adjacent the roll having the recessed pattern so that the slot is directed toward the roll carrying the recessed pattern. The outer shell has a pattern of openings disposed about its periphery and is rotatable about the inner shell.

In a preferred embodiment of the apparatus of the present invention, the first roll carrying the recessed pattern also comprises a stationary inner shell and a rotatable outer shell. The inner shell has a slot disposed transverse of its periphery at the position adjacent the roll having the hole pattern so that the slot is directed toward the roll carrying the hole pattern. The outer shell has a recessed pattern disposed about its periphery in the shape desired to be produced in the batt. Openings communicating with the inside of the roll are disposed in the recessed pattern. The outer shell is rotatable about the inner shell and vacuum is applied to the inside of the roll.

To produce a shaped batt, the loosely compacted fibrous material is passed between the nip formed by the oppositely rotating rolls. High-pressure air is directed from the inner shell of the one roll through the slot and through the openings in the outer shell to the recessed pattern of the other roll. This is accomplished as the batt passes through the nip and forms the batt into the shape of the pattern of openings and recessed pattern of the opposing rolls. If desired, the pattern in the rolls may be such as to cut across the full width of the batt to produce a plurality of individual batts. In some methods and apparatus of the present invention, combinations may be used to both shape the batt and cut the continuous batt into a plurality of individual batts or panels.

BRIEF DESCRIPTION OF THE DRAWINGS

FIG. 1 is a front view of apparatus according to the present invention;

FIG. 2 is a cross-sectional view taken through the plane of 2—2 of FIG. 1;

FIG. 3 is a cross-sectional view taken through a plane passing through the longitudinal axes of both rolls of the apparatus of the present invention; and FIG. 4 is a schematic side elevational view illustrating the method of the present invention.

DETAILED DESCRIPTION OF THE DRAWINGS

Referring to the drawings, in FIG. 1 there is shown a pair of rolls 10 and 11. The rolls are disposed adjacent one another and the axes of the rolls are parallel. The rolls are spaced apart to form nip 13. The upper roll 10 rotates in the direction as shown by the arrow on the shaft 14.

As is more clearly seen in FIGS. 2 and 3, the upper roll 10 comprises an outer shell 8 and an inner shell 9. The outer shell has a pair of spaced, circumferentially extending recesses 15 disposed about its periphery. The recesses cooperate to define a pattern that corresponds to the shape desired to be produced in the batt of loosely compacted fibrous material to be treated by the apparatus. Equally spaced, radially disposed passages extend through the wall of the outer shell to form openings or perforations 16 at the bottom of the recesses to aid in allowing for the escape and dissipation of the high-pressure air and pulp dust as will be described hereinafter. The inner shell 9 carries a slot 7 disposed transverse of its periphery at the position adjacent the bottom roll 11 as shown in the drawings. The outer shell 8 is rotatable about the inner shell 9. The shells are supported in standard bearings and the outer shell is driven by standard drive means, both of these items have been omitted from the drawings for the sake of clarity. Both the drive means and support bearings are well known in the art.

As is more clearly shown in FIGS. 2 and 3, the bottom roll 11 comprises a stationary inner shell 20 and a rotatable outer shell 21. The inner shell is hollow and air is fed to the inside of that shell through the opening 22 in shaft 23. At one point along the periphery of the shell there is a slot 24 running the width of the desired pattern and extending through the thickness of the shell. This is a transverse slot; that is, it runs the width of the roll as perhaps is more clearly seen in FIG. 3. This slot is disposed at that portion of the periphery closest to the upper roll and is so disposed as to direct the high-pressure air from the inside of the inner shell towards the upper or first roll. The rotatable outer shell has a pattern of openings 17 complimentary to the recessed pattern in the upper roll. The outer shell of the bottom roll is suitably geared to the upper roll so that it is rotating in the opposite direction as shown by the arrow in FIG. 1, but at the same peripheral linear speed as that of the upper roll. The technique for gearing and driving rolls in the manner described is well known in the art and the details have been omitted from the drawings for the purpose of clarity.

In operation, air is continuously fed through the opening in the stationary shaft in the bottom roll. The air passes through the nozzles in the stationary inner shell to the openings in the outer shell to produce jets of air to treat the batt in accordance with the pattern of openings as the batt passes between the nip formed by the pair of rolls.

In some embodiments of the present invention, the vacuum may be applied to the upper roll to aid in removing pulp dust from between the nip as the batt is being passed therethrough.

As the batt is being shaped, edge portions of the batt or scrap portions may be removed by air means. The unwanted portions may be blown away by appropriately positioned air jets or sucked away using vacuums. In either event, the scrap portions are recycled back to the starting batt forming operation.

In certain embodiments of the present invention, it may be desired that the shaped batt include a thin skin or lightly hydrogen bonded wood pulp fibers on one surface of the batt to improve certain of the absorbent characteristics of the batt. Such a skin is more fully described in U.S. Pat. Nos. 3,017,304 and 3,612,055. Such a skin may be formed on the batt either before or after the batt is shaped. If the skin is formed on the batt before it is shaped, it is then preferred that the skin surface be processed so that it is adjacent the air blowing roll for the most efficient operation.

The upper roll outer shell may be made from aluminum or a similar material, as desired. The width of the recessed pattern in the roll should be about ¼ inch. If the recess is too wide, you will lose control of the shaping, and if it is too narrow, the flow back or bounce back of air is disruptive to the operation. Depths of the recessed portion of about ¼ inch have been found satisfactory in carrying out the method of the present invention.

The bottom roll may be made of various materials. We have found that if the inner shell is made of aluminum and the outer shell stainless steel, satisfactory results are obtained. We have also found that if a brass insert 18 as shown in FIG. 2 is placed in the inner shell 20 to carry the slot, very satisfactory results are obtained. The reason for the brass insert is to allow for minimal spacing between the outer shell and the inner shell in the slot area to improve efficiency and use of air. By using the brass insert, the spacing between the brass and the outer stainless steel may be maintained at 0.003 to 0.005 inch and the remainder of the inner shell and outer shell may be spaced 0.01 inch and reduce wear of the shells.

Generally, air pressures of from about 40 to 60 lbs. per square inch have been found satisfactory in treating wood pulp batts weighing from about 10 grams to 75 grams and moving linearly at rates of speed from about 120 to about 500 feet per minute in accordance with the present invention. The higher the speed, of course, the higher the pressure usually required to shape the batt. The spacing between the rolls; that is, the nip through which the batt of loosely compacted fibrous material passes, should be just slightly less than the thickness of the batt.

The batt being treated comprises a mass of wood pulp fibers. Such fibers are short and are held together within the batt by frictional entanglement between adjacent fibers. This entanglement provides the batt with some slight integrity. The air as it passes through the batt to shape it separates the fibers and gently parts them from adjacent fibers without breaking or damaging the fibers. As this action is carried out in a confined nip and a very localized manner, the disruption of fibers in adjacent areas is kept to a minimum and the integrity of the shaped batt maintained.

It is preferred that the rolls not be the primary driving force of the batt and the batt be carried to the nip of the rolls and carried immediately away from the nip. In fact, in some instances, if a very open screen is used, the screen itself may be carried through the nip and carry the batt with it through the nip.

The patterns in the rolls may be varied greatly; i.e., they may be such that they shape the side edges of the batt being treated and/or cut the batt into a plurality of individual panels.

In carrying out the method of the present invention as schematically shown in FIG. 4, a pulp board 30 is fed to a standard grinding mill 31 and board 30 is ground to individualize the wood pulp fibers. The fibers 32 are laid on a permeable conveyer 33 in batt form and are loosely compacted by passing the batt under roll 34. The batt is passed through a first set of oppositely rotating rolls 35 and 36 in accordance with the present invention which shape the side edges of the batt. The shaped batt then passes through a second set of oppositely rotating rolls 37 and 38 in accordance with the present invention. The recessed pattern in roll 37 is a number of transverse lines disposed about the periphery of the roll. The air blowing pattern in roll 38 is also a number of transverse lines which compliment and cooperate with the transverse lines in roll 37 to periodically sever portions of the shaped batt. The severed portions are deposited on a second conveyor 39 which has a peripheral linear speed slightly in excess of the speed of the rotating rolls to produce a plurality of individual spaced apart shaped panels of loosely compacted fibrous material.

Though two separate pairs of rolls have been described, one pair to shape the batt and a second pair to sever the batt into individual panels, it should be appreciated that both steps could be accomplished with one pair of rolls. This is done including one or more transverse lines of very closely spaced openings in the pattern of the outer shell along with the desired shaping pattern of openings disposed about the periphery of the shell.

What is claimed is:

1. A method for continuously producing a plurality of individual absorbent panels from a continuous batt of loosely compacted short fibers comprising; passing a continuous batt of loosely compacted fibers through the nip formed by a pair of rotating surfaces, said surfaces rotating in opposite directions and at the same peripheral linear speed, said continuous batt being presented to said nip at the same linear speed as the peripheral linear speed of said surfaces, intermittently directing high-pressure air from one of said surfaces to a recessed portion of the other of said surfaces in the nip formed by the surfaces and across the face of said nip while passing the batt therebetween, to sever the continuous batt into a plurality of individual panels and conveying said panels away from the nip at a faster linear speed than the speed of the continuous batt being fed to said nip.

2. A method for shaping a batt of loosely compacted short fibers comprising; passing a batt of loose fibers through the nip formed by a pair of rotating surfaces, said surfaces rotating in opposite directions and at the same peripheral linear speed, continuously directing high-pressure air from one of said surfaces to a recess portion of the other of said surfaces at said nip in a pattern while passing the batt therebetween to shape the batt into the desired pattern.

3. A method according to claim 2 wherein the high-pressure air is directed from one of said surfaces to the other said surface and through said other surface while the batt passes between the nip formed by said surfaces.

4. A method for continuously producing a plurality of individual shaped absorbent panels from a continuous batt of loosely compacted short fibers comprising; passing a batt of loose fibers through the nip formed by a pair of rotating surfaces, said surfaces rotating in opposite directions and at the same peripheral linear speed, continuously directing high-pressure air from one of said surfaces to a recessed portion of the other of said surfaces at said nip in a pattern, said pattern including an intermittent line across the face of said nip, passing the batt between the nip to shape the batt and sever the continuous batt into a plurality of individual shaped panels and conveying said panels away from the nip at a faster linear speed than the speed of the continuous batt being fed to said nip.

5. A method for continuously producing a plurality of individual absorbent panels from a continuous batt of loosely compacted fibers comprising; passing a continuous batt of loosely compacted fibers through the nip formed by a pair of spaced moving surfaces, said surfaces moving in the same direction and at the same linear speed, said continuous batt being presented to said nip of surfaces at the same linear speed as the linear speed of said surfaces, intermittently directing high-pressure air from one of said surfaces to a recessed portion of the other of said surfaces in the nip formed by the surfaces while passing the batt therebetween, to sever the continuous batt into a plurality of individual panels and conveying said panels away from the spaced moving surfaces at a faster linear speed than the speed of the continuous batt being fed to said moving surfaces.

6. A method for shaping a batt of loosely compacted fibers comprising; passing a batt of loose fibers through the nip formed by a pair of spaced moving surfaces, said surfaces moving in the same direction and at the same linear speed, continuously directing high-pressure air from one of said surfaces to a recessed portion of the other of said surfaces in a pattern while passing the batt therebetween to shape the batt into the desired pattern.

7. A method for continuously producing a plurality of individual shaped absorbent panels from a continuous batt of loosely compacted fibers comprising; passing a batt of loose fibers through the nip formed by a pair of spaced moving surfaces, said surfaces moving in the same direction and at the same linear speed, continuously directing high-pressure air from one of said surfaces to a recessed portion of said surfaces at said nip in a pattern, said pattern including an intermittent line across the face of said nip, passing the batt through said space to shape the batt including severing the continuous batt into a plurality of individual shaped panels and conveying said panels away from the nip of said moving surfaces at a faster linear speed than the speed of the continuous batt being fed to said nip.

* * * * *